United States Patent [19]

Blacklock et al.

[11] Patent Number: 4,968,815

[45] Date of Patent: Nov. 6, 1990

[54] SYNTHESIS OF (S)-3-(THIEN-2-YLTHIO)BUTYRIC ACID ANALOGS

[75] Inventors: Thomas J. Blacklock, Clark; Ichiro Shinkai, Westfield, both of N.J.

[73] Assignee: Merck & Co., Inc., Rahway, N.J.

[21] Appl. No.: 510,805

[22] Filed: Apr. 16, 1990

[51] Int. Cl.$^5$ .......................................... C07D 333/32
[52] U.S. Cl. ....................................................... 549/66
[58] Field of Search ........................................... 549/66

[56] References Cited

U.S. PATENT DOCUMENTS 4,021,450  5/1977  Ahrens et al. .......................... 549/66
4,245,107  1/1981  Shibuya et al. ......................... 549/66
4,797,413  1/1989  Baldwin et al. ........................ 514/432

*Primary Examiner*—Alan Siegel
*Attorney, Agent, or Firm*—William H. Nicholson; Joseph F. DiPrima

[57] ABSTRACT

(S)-3-(thien-2-ylthio)butyric acid analogs are intermediates in the synthesis of the chiral (S,S)-5,6-dihydro-4-ethylamino-6-methyl-4H-thieno[2,3-b]thiopyran-2-sulfonamide-7,7-dioxide and analogs thereof, topically effective carbonic anhydrase inhibitors useful in the treatment of ocular hypertension and glaucoma. They are prepared by condensation of 2-mercaptothiophene and (R)-(+)-β-methyl-β-propiolactone or an analog thereof.

4 Claims, No Drawings

SYNTHESIS OF (S)-3-(THIEN-2-YLTHIO)BUTYRIC ACID ANALOGS

SUMMARY OF THE INVENTION

This invention is concerned with a novel process for preparation of a chiral compound of structural formula I:

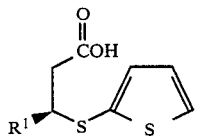

Compound I is a key intermediate in the synthesis of the compound of formula:

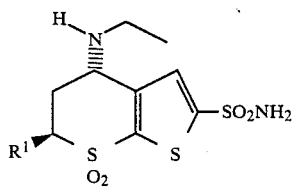

which is a carbonic anhydrase inhibitor topically effective in the treatment of ocular hypertension and glaucoma.

The novel process for preparing Compound I comprises treating a nucleophile of structure II with a compound of structure III as shown:

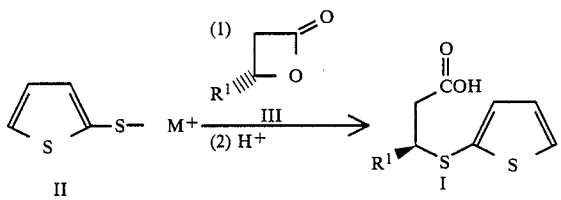

wherein the R groups are as hereinafter defined.

BACKGROUND OF THE INVENTION

The carbonic anhydrase inhibitor described above is disclosed in U.S. Pat. No. 4,797,413 which also discloses a process for preparing the racemic modification of the alkyl 3-(thien-2-ylthio)butyrate and its homologs. The prior art process comprises addition of the 2-thienyl-thiol across the double bond of a substituted acrylic acid:

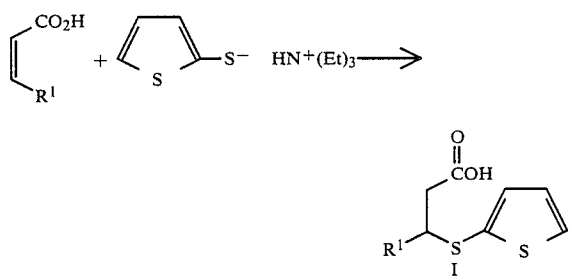

followed by synthesis of the final diastereomeric product, the isomers of which must be separated and each resolved to obtain the most active (S,S)-enantiomer. The isomer separations result in an automatic loss of the bulk of the chemical product.

It is therefore an object of this invention to provide a chiral intermediate for the synthesis of a chiral final product more economically than previously possible.

It is also an object of this invention to provide a process for the synthesis of the chiral intermediate.

DETAILED DESCRIPTION OF THE INVENTION

The novel process of this invention comprises the condensation of thienyl-2-thiol with a chiral propiolactone of structure III and may be represented as follows:

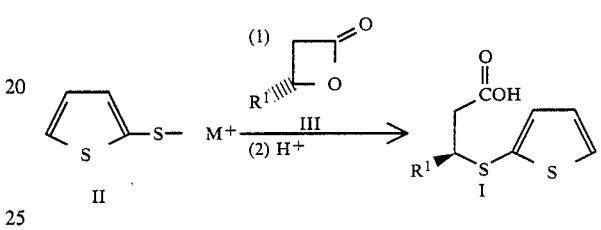

wherein; $R^1$ is $C_{1-4}$alkyl, preferably methyl, or $C_{1-4}$alkoxy-$C_{1-4}$alkyl especially ethoxyethyl, and $M^+$ is $(C_2H_5)_3 NH^+$ or $Li^+$.

The condensation is conducted in an ethereal solvent such as THF, diethyl ether or 1,2-dimethoxyethane at about 10°–40° C., preferably about 20°–25° C. until the reaction is substantially complete in about 2–5 hours.

EXPERIMENTAL

To a magnetically-stirred 25 mL round-bottomed flask blanketed with nitrogen was charged 2-mercapto-thiophene (0.73 g, 6.29 mmol) in tetrahydrofuran (7 mL, K.F. <0.1 mg/mL) at 25° C. Triethylamine (0.87 mL, 6.29 mmol) was injected and the reaction mixture was stirred for 10 minutes to complete salt formation. To this mixture was added (R)-(+)-β-methyl-β-propiolactone (0.54 g, 6.29 mmol) in one portion and the reaction mixture was stirred at 25° C. for approximately 3 hours. When complete, the mixture was stripped of solvent on a rotary evaporator at 25° C. and diluted with ethyl acetate (10 mL) and water (10 mL). The pH of the mixture was then adjusted to 2.0 with 5N hydrochloric acid and the layers separated. The upper ethyl acetate product layer was dried over sodium sulfate and concentrated to an oil on a rotary evaporator. Silica gel chromatography (10% ethyl acetate/hexanes) afforded 1.19 g of (S)-3-(2-thienylthio)butyric acid (94%).

$^1$H NMR (CDCl$_3$) 7.42 (M,1H), 7.19 (M,1H), 7.03 (M,1H), 3.38 (M,1H), 2.72 (dd, 1H, J=16.0, J=6.4 Hz), 2.48 (dd, 1H, J=16.0, J=8.0 Hz), 1.35 (d, 3H, J=6.8 Hz);

$^{13}$C NMR (CDCl$_3$) 177.5(s), 136.4(s), 130.9(s), 130.6(s), 127.7(s), 41.4(s), 41.3(s), 20.6(s);

HRMS calcd. for $C_8H_{10}O_2S_2$ (M+) 202.0122, Found 202.0121

Employing the procedures substantially as described in the foregoing experimental but substituting for the (R)-(+)-β-methyl-β-propiolactone used therein comparable amounts of the β-substituted lactones shown in the following table, there are produced the (S)-3-(2-thienyl-thio)alkanoic acids also described in the following table:

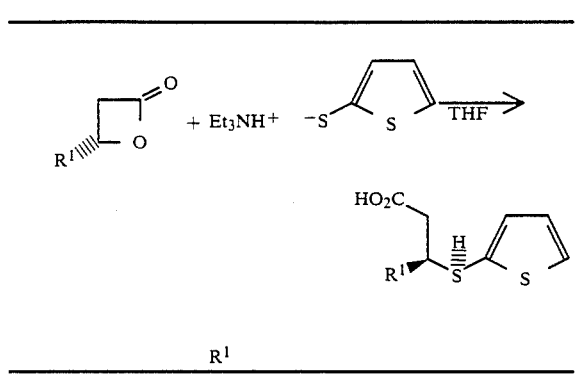

| $R^1$ |
| --- |
| $CH_3O(CH_2)_2-$ |
| $C_2H_5O(CH_2)_2-$ |
| $C_3H_7O(CH_2)_2-$ |
| $CH_3O(CH_2)_3-$ |
| $C_2H_5O(CH_2)_2-$ |
| $C_2H_5O(CH_2)_3-$ |
| $C_2H_5-$ |
| $C_3H_7-$ |

What is claimed is:

1. A process for the preparation of a compound of structural formula I:

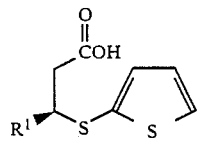

wherein $R^1$ is $C_{1-4}$alkyl or $C_{1-4}$alkoxy-$C_{1-4}$alkyl; which comprises treating a compound of structural formula II:

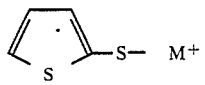

wherein $M^+$ is $(C_2H_5)_3NH^+$ or $Li^+$ with a compound of structural formula III:

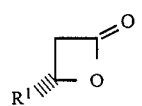

in an ethereal solvent at a temperature of about 10° to 40° C. for about 2-5 hours.

2. The process of claim 1 wherein the ethereal solvent is THF and the temperature is 20°-25° C.

3. The process of claim 1 wherein $R^1$ is methyl, and $M^+$ is $(C_2H_5)_3NH^+$.

4. The process of claim 2 wherein $R^1$ is methyl, and $M^+$ is $(C_2H_5)_3NH^+$.

* * * * *